(12) United States Patent
McCauley et al.

(10) Patent No.: US 8,377,443 B2
(45) Date of Patent: Feb. 19, 2013

(54) ANTIBODIES TO MATRIX METALLOPROTEINASE 9

(75) Inventors: Scott McCauley, Brisbane, CA (US); Maria Vaysberg, Foster City, CA (US)

(73) Assignee: Gilead Biologics, Inc., Foster City, CA (US)

( * ) Notice: Subject to any disclaimer, the term of this patent is extended or adjusted under 35 U.S.C. 154(b) by 0 days.

(21) Appl. No.: 13/219,523

(22) Filed: Aug. 26, 2011

(65) Prior Publication Data

US 2012/0135004 A1 May 31, 2012

Related U.S. Application Data

(60) Provisional application No. 61/377,886, filed on Aug. 27, 2010.

(51) Int. Cl.
*C07K 16/18* (2006.01)
*A61K 39/395* (2006.01)
(52) U.S. Cl. .................................. 424/141.1; 530/388.1
(58) Field of Classification Search .................. None
See application file for complete search history.

(56) References Cited

U.S. PATENT DOCUMENTS

| | | | |
|---|---|---|---|
| 4,816,567 | A | 3/1989 | Cabilly et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 7,101,975 | B1 | 9/2006 | Brooks et al. |
| 7,524,938 | B2 | 4/2009 | Sagi et al. |
| 7,566,449 | B2 | 7/2009 | Brooks et al. |
| 2002/0159971 | A1 | 10/2002 | Houde et al. |
| 2004/0141982 | A1 | 7/2004 | Lust et al. |
| 2004/0175817 | A1 | 9/2004 | Jepson et al. |
| 2005/0287148 | A1 | 12/2005 | Chatterjee et al. |
| 2007/0172482 | A1 | 7/2007 | Sagi et al. |
| 2009/0186031 | A1 | 7/2009 | Wood et al. |
| 2009/0208510 | A1 | 8/2009 | Sagi et al. |
| 2009/0297449 | A1 | 12/2009 | Devy |
| 2009/0311245 | A1 | 12/2009 | Devy et al. |

FOREIGN PATENT DOCUMENTS

| | | |
|---|---|---|
| EP | 0 685 557 | 8/1998 |
| WO | WO-01/04157 | 1/2001 |
| WO | WO-02/066057 | 8/2002 |
| WO | WO-03/006006 | 1/2003 |
| WO | WO-03/044058 | 5/2003 |
| WO | WO-2004/022096 | 3/2004 |
| WO | WO-2004/076614 | 9/2004 |
| WO | WO-2006/037513 | 4/2006 |
| WO | WO-2007/005426 | 1/2007 |
| WO | WO-2007/094842 | 8/2007 |
| WO | WO-2007/144781 | 12/2007 |
| WO | WO-2008/088864 | 7/2008 |
| WO | WO-2008/154439 | 12/2008 |
| WO | WO-2009/022328 | 2/2009 |
| WO | WO-2009/111450 | 9/2009 |
| WO | WO-2009/111508 | 9/2009 |
| WO | WO-2010/048432 | 4/2010 |
| WO | WO-2010/059543 | 5/2010 |
| WO | WO-2011/092700 | 8/2011 |

OTHER PUBLICATIONS

BioMosaics, Anti-Human Active Matrix Metalloproteinase 9 Antibody, Jul. 15, 2009, retrieved from the Internet Feb. 12, 2012: <http://www.biomosaics.com/pdfs/B2057M.pdf>.

Hu et al., "Inhibitors of gelatinase B/matrix metalloproteinase-9 activity comparison of a peptidomimetic and polyhistidine with single-chain derivatives of a neutralizing monoclonal antibody," Biochem. Pharmacol. (2004) 67(5):1001-1009.

International Search Report and Written Opinion for PCT/US11/49448, mailed Jun. 22, 2012, 12 pages.

Nagase et al., "Structure and function of matrix metalloproteinases and TIMPs," Cardiovasc. Res. (2006) 69(3):562-573.

Tochowicz et al., "Crystal structures of MMP-9 complexes with five inhibitors: contribution of the flexible Arg424 side-chain to selectivity," J. Mol. Biol. (2007) 371(4):989-1006.

Vector Laboratories, Product Specifications, Antibody to Matrix Metalloproteinase 9, 2004, retrieved from the Internet Feb. 12, 2012: <http://www.vectorlabs.com/data/protocols/VPM644.pdf>.

Visse et al., "Matrix metalloproteinases and tissue inhibitors of metalloproteinases: structure, function, and biochemistry," Circ. Res. (2003) 92(8):827-839.

Angal et al., "A Single Amino Acid Substitution Abolishes the Heterogeneity of Chimeric Mouse/Human (IgG4) Antibody," Molec. Immunol. (1993) 30:105-108.

Boerner et al., "Production of Antigen-Specific Human Monoclonal Antibodies from in Vitro-Primed Human Splenocytes," J. Immunol. (1991) 147:86-95.

Fishwild et al., "High-Avidity Human IgGK Monoclonal Antibodies from a Novel Strain of Minilocus Transgenic Mice," Nature Biotechnology (1996) 14:845-851.

Hoogenboom et al., "By-Passing Immunisation Human Antibodies from Synthetic Repertoires of Germline $V_H$ Gene Segments Rearranged in Vitro," J. Mol. Biol. (1992) 227:381-388.

Hu et al., "Matrix Metalloproteinase Inhibitors as Therapy for Inflammatory and Vascular Diseases," Nature Reviews: Drug Discovery (2007) 6:480-498.

Jones et al., "Replacing the Complementarity—Determining Regions in a Human Antibody with Those from a Mouse," Nature (1986) 321:522-525.

(Continued)

*Primary Examiner* — Prema Mertz
(74) *Attorney, Agent, or Firm* — Morrison & Foerster LLP

(57) ABSTRACT

The present disclosure provides compositions and methods of use involving binding proteins, e.g., antibodies and antigen-binding fragments thereof, that bind to the matrix metalloproteinase-9 (MMP9) protein (MMP9 is also known as gelatinase-B), wherein the binding proteins comprise an immunoglobulin (Ig) heavy chain (or functional fragment thereof) and an Ig light chain (or functional fragment thereof).

7 Claims, 3 Drawing Sheets

OTHER PUBLICATIONS

Lonberg et al., "Antigen-Specific Human Antibodies from Mice Comprising Four Distinct Genetic Modifications," Nature (1994) 368:856-859.

Lonberg et al., "Human Antibodies from Transgenic Mice," Intern. Rev. Immunol. (1995) 13:65-93.

Marks et al., "By-Passing Immunization Human Antibodies from V-gene Libraries Displayed on Phage," J. Mol. Biol. (1991) 222:581-597.

Marks et al., "By-Passing Immunization: Building High Affinity Human Antibodies by Chain Shuffling," Bio/Technology (1992) 10:779-783.

Martens et al., "A Monoclonal Antibody Inhibits Gelatinase B/MMP-9 by Selective Binding to Part of the Catalytic Domain and Not to the Fibronectin or Zinc Binding Domains," Biochimica et Biophysica Acta (2007) 1770:178-186.

Morrison, "Success in Specification," Nature (1994) 368:812-813.

Neuberger, "Generating High-Avidity Human Mabs in Mice," Nature Biotechnology (1996) 14:826.

Presta, "Antibody Engineering," Curr. Op. Struct. Biol. (1992) 2:593-596.

Riechmann et al., "Reshaping Human Antibodies for Therapy," Nature (1988) 332:323-329.

Verhoeyen et al., "Reshaping Human Antibodies: Grafting an Antilysozyme Activity," Science (1988) 239:1534-1536.

Zapata et al., "Engineering Linear F(ab')$_2$ Fragments for Efficient Production in *Escherichia coli* and Enhanced Antiproliferative Activity," Protein Eng. (1995) 8(10):1057-1062.

Carter et al., "Potent Antibody Therapeutics by Design," Nature Reviews, Immunology (2006) 6(7):343-357.

Davies et al., "Affinity Improvement of Single Antibody VH Domains: Residues in All Three Hypervariable Regions Affect Antigen Binding," Immunotechnology (1996) 2(3):169-179.

Holt et al., "Domain Antibodies: Proteins for Therapy," Trends in Biotechnology (2003) 21(11):484-490.

International Search Report and Written Opinion of the International Searching Authority for International Patent Application No. PCT/US2012/027160, mailed Nov. 8, 2012, 19 pages.

Wark et al., "Latest Technologies for the Enhancement of Antibody Affinity," Advanced Drug Delivery Reviews (2006) 58(5-6):657-670.

FIGURE 1

Anti-MMP9 humanized heavy chains

```
AB0041    QVQLKESGPG  LVAPSQSLSI  TCTVSGFSLL  SYGVHWVRQP  PGKGLEWLGV
VH1       QVQLQESGPG  LVKPSETLSL  TCTVSGFSLL  SYGVHWVRQP  PGKGLEWLGV
VH2       QVQLQESGPG  LVKPSETLSL  TCTVSGFSLL  SYGVHWVRQP  PGKGLEWLGV
VH3       QVQLQESGPG  LVKPSETLSL  TCTVSGFSLL  SYGVHWVRQP  PGKGLEWLGV
VH4       QVQLQESGPG  LVKPSETLSL  TCTVSGFSLL  SYGVHWVRQP  PGKGLEWLGV

AB0041    IWTGGTTNYN  SALMSRLSIS  KDDSKSQVFL  KMNSLQTDDT  AIYYCARYYY
VH1       IWTGGTTNYN  SALMSRLTIS  KDDSKSTVYL  KMNSLKTEDT  AIYYCARYYY
VH2       IWTGGTTNYN  SALMSRLTIS  KDDSKNTVYL  KMNSLKTEDT  AIYYCARYYY
VH3       IWTGGTTNYN  SALMSRFTIS  KDDSKNTVYL  KMNSLKTEDT  AIYYCARYYY
VH4       IWTGGTTNYN  SALMSRFTIS  KDDSKNTLYL  KMNSLKTEDT  AIYYCARYYY

AB0041    GMDYWGQGTS  VTVSS   (SEQ ID NO:3)
VH1       GMDYWGQGTS  VTVSS   (SEQ ID NO:5)
VH2       GMDYWGQGTL  VTVSS   (SEQ ID NO:6)
VH3       GMDYWGQGTL  VTVSS   (SEQ ID NO:7)
VH4       GMDYWGQGTL  VTVSS   (SEQ ID NO:8)
```

FIGURE 2

Anti-MMP9 humanized light chains

```
AB0041    DIVMTQSHKF MSTSVGDRVS ITCKASQDVR NTVAWYQQKT GQSPKLLIYS
Vk1       DIVMTQSPSF LSASVGDRVT ITCKASQDVR NTVAWYQQKT GKAPKLLIYS
Vk2       DIVMTQSPSS LSASVGDRVT ITCKASQDVR NTVAWYQQKP GKAPKLLIYS
Vk3       DIQMTQSPSS LSASVGDRVT ITCKASQDVR NTVAWYQQKP GKAPKLLIYS
Vk4       DIQMTQSPSS LSASVGDRVT ITCKASQDVR NTVAWYQQKP GKAPKLLIYS

AB0041    SSYRNTGVPD RFTGSGSGTD FTFTISSVQA EDLAVYFCQQ HYITPYTFGG
Vk1       SSYRNTGVPD RFTGSGSGTD FTLTISSLQA EDVAVYFCQQ HYITPYTFGG
Vk2       SSYRNTGVPD RFTGSGSGTD FTLTISSLQA EDVAVYFCQQ HYITPYTFGG
Vk3       SSYRNTGVPD RFSGSGSGTD FTLTISSLQA EDVAVYFCQQ HYITPYTFGG
Vk4       SSYRNTGVPD RFSGSGSGTD FTLTISSLQA EDVAVYYCQQ HYITPYTFGG

AB0041    GTKLEIK   (SEQ ID NO:4)
Vk1       GTKVEIK   (SEQ ID NO:9)
Vk2       GTKVEIK   (SEQ ID NO:10)
Vk3       GTKVEIK   (SEQ ID NO:11)
Vk4       GTKVEIK   (SEQ ID NO:12)
```

ANTIBODIES TO MATRIX METALLOPROTEINASE 9

CROSS REFERENCE TO RELATED APPLICATIONS

This application claims priority benefit of U.S. provisional application Ser. No. 61/377,886, filed Aug. 27, 2011, which application is incorporated herein by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 246102008000Seqlist.txt | Oct. 20, 2011 | 38,945 bytes |

FIELD

This disclosure is in the field of extracellular enzymes, extracellular matrix enzymes, proteases and immunology.

INTRODUCTION

Matrix metalloproteinases (MMPs) are a family of extracellular enzymes involved in forming and remodeling the extracellular matrix. These enzymes contain a conserved catalytic domain in which a zinc atom is coordinated by three histidine residues. Currently, over 20 members of this family are known, organized into a number of groups including collagenases, gelatinases, stromelysins, matrilysins, enamelysins and membrane MMPs.

MMP2 and MMP9 belong to the gelatinase group of matrix metalloproteinases. Besides containing signal peptide, propeptide, catalytic, zinc-binding and heamopexin-like domains common to most MMPs, the gelatinases also contain a plurality of fibronectin-like domains and an O-glycosylated domain.

Abnormal activity of certain MMPs has been shown to play a role in tumor growth, metastasis, inflammation and vascular disease. See, for example, Hu et al. (2007) *Nature Reviews: Drug Discovery* 6:480-498. Because of this, it can be desirable to inhibit the activity of one or more MMPs in certain therapeutic settings. However, the activity of certain other MMPs is often required for normal function. Since most MMP inhibitors are targeted to the conserved catalytic domain and, as a result, inhibit a number of different MMPS, their therapeutic use has caused side effects due to the inhibition of essential, non-pathogenically-related MMPs.

Despite this problem, it has proven difficult to develop inhibitors that are specific to a particular MMP, because inhibition of enzymatic activity generally requires that the inhibitor be targeted to the catalytic domain. Consequently, most inhibitors of matrix metalloproteinase enzymatic activity are likely to react with more than one MMP, due to homologies in their catalytic domains. Thus, there remains a need for therapeutic reagents that specifically inhibit the catalytic activity of a single MMP, and that do not react with other MMPs.

SUMMARY

The present disclosure provides compositions and methods of use involving binding proteins, e.g., antibodies and antigen-binding fragments thereof, that bind to the matrix metalloproteinase-9 (MMP9) protein (MMP9 is also known as gelatinase-B), wherein the binding proteins comprise an immunoglobulin (Ig) heavy chain (or functional fragment thereof) and an Ig light chain (or functional fragment thereof). The disclosure further provides MMP9 binding proteins that bind specifically to MMP9 and not to other, related matrix metalloproteinases. Such MMP9 binding proteins find use in applications in which it is necessary or desirable to obtain specific modulation (e.g., inhibition) of MMP9, e.g., without directly affecting the activity of other matrix metalloproteinases. Thus, in certain embodiments of the present disclosure an anti-MMP9 antibody is a specific inhibitor of the activity of MMP9. In particular, the MMP9 binding proteins disclosed herein will be useful for inhibition of MMP9 while allowing normal function of other, related matrix metalloproteinases.

Accordingly, the present disclosure provides, inter alia:

1. A MMP9 binding protein comprising an immunoglobulin heavy chain or functional fragment thereof, and an immunoglobulin light chain or functional fragment thereof, wherein the protein does not bind to a matrix metalloproteinase other than MMP9.

2. The protein of embodiment 1, wherein the heavy chain comprises a complementarity-determining region (CDR) selected from one or more of SEQ ID NOs: 13-15, and the light chain comprises a CDR selected from one or more of SEQ ID NOs: 16-18.

3. The protein of embodiment 2, wherein the heavy chain comprises a variable region selected from the group consisting of SEQ ID NOs: 3 or 5-8, and the light chain comprises a variable region selected from the group consisting of SEQ ID NOs: 4 or 9-12.

4. The protein of embodiment 1, wherein the heavy chain is an IgG.

5. The protein of embodiment 1, wherein the light chain is a kappa chain.

6. The protein of embodiment 1, wherein the binding of the protein to MMP9 inhibits the enzymatic activity of MMP9.

7. The protein of embodiment 6, wherein the inhibition is non-competitive.

8. The protein of embodiment 1, wherein the heavy chain is encoded by a polynucleotide having a nucleotide sequence selected from the group consisting of SEQ ID NOs: 19-22 and the light chain is encoded by a polynucleotide having a nucleotide sequence selected from the group consisting of SEQ ID NOs: 23-26.

9. A vector comprising one or more polynucleotides having a nucleotide sequence selected from the group consisting of SEQ ID NOs: 19-26.

10. A cell comprising the vector of embodiment 9.

11. A pharmaceutical composition comprising the protein of embodiment 1.

12. A pharmaceutical composition comprising the vector of embodiment 9.

13. A pharmaceutical composition comprising the cell of embodiment 10.

BRIEF DESCRIPTION OF THE DRAWINGS

FIG. 1 shows the amino acid sequence of the heavy chain variable region of a mouse monoclonal anti-MMP9 antibody (AB0041), along with the amino acid sequences of humanized variants of heavy chain (VH1-VH4), aligned to show differences in framework amino acid sequence resulting from humanization. CDRs are shown in italics, and amino acids that are different in the humanized variants, compared to the parent mouse monoclonal, are underlined.

FIG. 2 shows the amino acid sequence of the light chain variable region of a mouse monoclonal anti-MMP9 antibody (AB0041), along with the amino acid sequences of humanized variants of this light chain (VH1-VH4), aligned to show differences in framework amino acid sequence resulting from humanization. CDRs are shown in italics, and amino acids that are different in the humanized variants, compared to the parent mouse monoclonal, are underlined.

DETAILED DESCRIPTION

Figure 3:
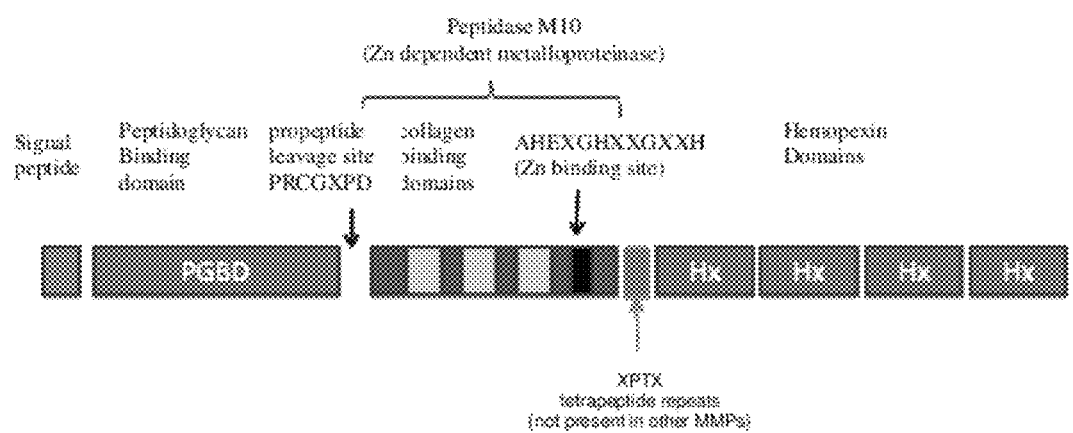
FIG. 3 shows a schematic diagram of the MMP9 protein.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3$^{rd}$ edition, John Wiley & Sons, Hoboken, N.J., 2008; Sambrook, J. et al., "Molecular Cloning: A Laboratory Manual," 3$^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4$^{th}$ edition, John Wiley & Sons, Somerset, N.J., 2000; and the series "Methods in Enzymology," Academic Press, San Diego, Calif.

See also, for example, "Current Protocols in Immunology," (R. Coico, series editor), Wiley, last updated August 2010.

MMP9 Binding Proteins

The present disclosure provides binding proteins, e.g., antibodies and antigen-binding fragments thereof, that bind to the matrix metalloproteinase-9 (MMP9) protein (MMP9 is also known as gelatinase-B), The binding proteins of the present disclosure generally comprise an immunoglobulin (Ig) heavy chain (or functional fragment thereof) and an Ig light chain (or functional fragment thereof).

The disclosure further provides MMP9 binding proteins that bind specifically to MMP9 and not to other matrix metalloproteinases such as MMP1, MMP2, MMP3, MMP7, MMP9, MMP10, MMP12, MMP13. Such specific MMP9 binding proteins are thus generally not significantly or detectably crossreactive with non-MMP9 matrix metalloproteinases. MMP9 binding proteins that specifically bind MMP9 find use in applications in which it is necessary or desirable to obtain specific modulation (e.g., inhibition) of MMP9, e.g., without directly affecting the activity of other matrix metalloproteinases.

In certain embodiments of the present disclosure an anti-MMP9 antibody is an inhibitor of the activity of MMP9, and can be a specific inhibitor of MMP9. In particular, the MMP9 binding proteins disclosed herein will be useful for inhibition of MMP9 while allowing normal function of other, related matrix metalloproteinases. "An inhibitor of MMP" or "inhibitor of MMP9 activity" can be an antibody or an antigen binding fragment thereof that directly or indirectly inhibits activity of MMP9, including but not limited to enzymatic processing, inhibiting action of MMP9 on it substrate (e.g., by inhibiting substrate binding, substrate cleavage, and the like), and the like.

The present disclosure also provides MMP9 binding proteins that specifically bind to non-mouse MMP9, such as human MMP9, Cynomolgus monkey MMP9, and rat MMP9.

The present disclosure also provides MMP9 binding proteins (e.g., anti-MMP9 antibodies and functional fragments thereof) that act as non-competitive inhibitors. A "non-competitive inhibitor" refers to an inhibitor binds at site away from substrate binding site of an enzyme, and thus can bind the enzyme and effect inhibitory activity regardless of whether or not the enzyme is bound to its substrate, Such non-competitive inhibitors can, for example, provide for a level of inhibition that can be substantially independent of substrate concentration.

MMP9 binding proteins (e.g., antibodies and functional fragments thereof) of the present disclosure include those that bind MMP9, particularly human MMP9, and having a heavy chain polypeptide (or functional fragment thereof) that has at least about 80%, 85%, 90%, 95% or more amino acid sequence identity to a heavy chain polypeptide disclosed herein.

MMP9 binding proteins (e.g., antibodies and functional fragments thereof) of the present disclosure include those that bind MMP9, particularly human MMP9, and having a light polypeptide (or functional fragment thereof) that has at least about 80%, 85%, 90%, 95% or more amino acid sequence identity to a heavy chain polypeptide disclosed herein.

MMP9 binding proteins (e.g., antibodies and functional fragments thereof) of the present disclosure include those that bind MMP9, particularly human MMP9, and have a heavy chain polypeptide (or functional fragment thereof) having the complementarity determining regions ("CDRs") of heavy chain polypeptide and the CDRs of a light chain polypeptide (or functional fragment thereof) as disclosed herein.

"Homology" or "identity" or "similarity" as used herein in the context of nucleic acids and polypeptides refers to the relationship between two polypeptides or two nucleic acid molecules based on an alignment of the amino acid sequences or nucleic acid sequences, respectively. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. In comparing two sequences, the absence of residues (amino acids or nucleic acids) or presence of extra residues also decreases the identity and homology/similarity.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least about 20, 25, 30, 35, 40, 45, 50, 55, 60, 65 or more amino acids or nucleotides in length, and can be up to the full-length of the reference amino acid or nucleotide. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (www.ncbi.nlm.nih.gov). Further exemplary algorithms include ClustalW (Higgins D., et al. (1994) Nucleic Acids Res 22: 4673-4680), available at www.ebi.ac.uk/Tools/clustalw/index.html.

Residue positions which are not identical can differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

Accordingly, the present disclosure provides, for example, antibodies or antigen binding fragments thereof, comprising a heavy chain variable region polypeptide having at least 80%, 85%, 90%, 95%, or greater amino acid sequence identity to an amino acid sequence of a heavy chain variable region described herein (e.g., SEQ ID NOS:1 or 5-8), and a variable light chain polypeptide having at least 80%, 85%, 90%, 95%, or greater amino acid sequence identity to an amino acid sequence of a light chain polypeptide as set forth herein (e.g., SEQ ID NOS:2 or 9-12).

Examples of anti-MMP9 antibodies of the present disclosure are described in more detail below.

Antibodies

MMP9 binding proteins including antibodies and functional fragments thereof. As used herein, the term "antibody" means an isolated or recombinant polypeptide binding agent that comprises peptide sequences (e.g., variable region sequences) that specifically bind an antigenic epitope. The term is used in its broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to Fv, scFv, Fab, Fab' F(ab')$_2$ and Fab$_2$, so long as they exhibit the desired biological activity. The term "human antibody" refers to antibodies containing sequences of human origin, except for possible non-human CDR regions, and does not imply that the full structure of an immunoglobulin molecule be present, only that the antibody has minimal immunogenic effect in a human (i.e., does not induce the production of antibodies to itself).

An "antibody fragment" comprises a portion of a full-length antibody, for example, the antigen binding or variable region of a full-length antibody. Such antibody fragments may also be referred to herein as "functional fragments" or "antigen-binding fragments". Examples of antibody fragments include Fab, Fab', F(ab')$_2$, and Fv fragments; diabodies; linear antibodies (Zapata et al. (1995) Protein Eng. 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three complementarity-determining regions (CDRs) of each variable domain interact to define an antigen-binding site on the surface of the $V_H$-$V_L$ dimer. Collectively, the six CDRs confer antigen-binding specificity to the antibody. However, even a single variable domain (or an isolated $V_H$ or $V_L$ region comprising only three of the six CDRs specific for an antigen) has the ability to recognize and bind antigen, although generally at a lower affinity than does the entire $F_v$ fragment.

The "$F_{ab}$" fragment also contains, in addition to heavy and light chain variable regions, the constant domain of the light chain and the first constant domain (CH$_1$) of the heavy chain. Fab fragments were originally observed following papain digestion of an antibody. Fab' fragments differ from Fab fragments in that F(ab') fragments contain several additional residues at the carboxy terminus of the heavy chain CH$_1$ domain, including one or more cysteines from the antibody hinge region. F(ab')$_2$ fragments contain two Fab fragments joined, near the hinge region, by disulfide bonds, and were originally observed following pepsin digestion of an antibody. Fab'-SH is the designation herein for Fab' fragments in which the cysteine residue(s) of the constant domains bear a free thiol group. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to five major classes: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun, in *The Pharmacology of Monoclonal Antibodies*, vol. 113 (Rosenburg and Moore eds.) Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain, thereby creating two antigen-binding sites. Diabodies are additionally described, for example, in EP 404,097; WO 93/11161 and Hollinger et al. (1993) *Proc. Natl. Acad. Sci. USA* 90:6444-6448.

An "isolated" antibody is one that has been identified and separated and/or recovered from a component of its natural environment. Components of its natural environment may include enzymes, hormones, and other proteinaceous or non-proteinaceous solutes. In some embodiments, an isolated antibody is purified (1) to greater than 95% by weight of antibody as determined by the Lowry method, for example, more than 99% by weight, (2) to a degree sufficient to obtain at least 15 residues of N-terminal or internal amino acid sequence, e.g., by use of a spinning cup sequenator, or (3) to homogeneity by gel electrophoresis (e.g., SDS-PAGE) under reducing or nonreducing conditions, with detection by Coomassie blue or silver stain. The term "isolated antibody" includes an antibody in situ within recombinant cells, since at least one component of the antibody's natural environment will not be present. In certain embodiments, isolated antibody is prepared by at least one purification step.

As used herein, "immunoreactive" refers to antibodies or fragments thereof that are specific to a sequence of amino acid residues ("binding site" or "epitope"), yet if are cross-reactive to other peptides/proteins, are not toxic at the levels at which they are formulated for administration to human use. "Epitope" refers to that portion of an antigen capable of forming a binding interaction with an antibody or antigen binding fragment thereof. An epitope can be a linear peptide sequence (i.e., "continuous") or can be composed of noncontiguous amino acid sequences (i.e., "conformational" or "discontinuous"). The term "preferentially binds" means that the binding agent binds to the binding site with greater affinity than it binds unrelated amino acid sequences.

Anti-MMP9 antibodies can be described in terms of the CDRs of the heavy and light chains. As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR Definitions | | | |
|---|---|---|---|
| | Kabat[1] | Chothia[2] | MacCallum[3] |
| $V_H$CDR1 | 31-35 | 26-32 | 30-35 |
| $V_H$CDR2 | 50-65 | 53-55 | 47-58 |
| $V_H$CDR3 | 95-102 | 96-101 | 93-101 |
| $V_L$CDR1 | 24-34 | 26-32 | 30-36 |
| $V_L$CDR2 | 50-56 | 50-52 | 46-55 |
| $V_L$CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

In some embodiments, an antibody is a humanized antibody or a human antibody. Humanized antibodies include human immunoglobulins (recipient antibody) in which residues from a complementary-determining region (CDR) of the recipient are replaced by residues from a CDR of a non-human species (donor antibody) such as mouse, rat or rabbit having the desired specificity, affinity and capacity. Thus, humanized forms of non-human (e.g., murine) antibodies are chimeric immunoglobulins which contain minimal sequence derived from non-human immunoglobulin. The non-human sequences are located primarily in the variable regions, particularly in the complementarity-determining regions (CDRs). In some embodiments, Fv framework residues of the human immunoglobulin are replaced by corresponding non-human residues. Humanized antibodies can also comprise residues that are found neither in the recipient antibody nor in the imported CDR or framework sequences. In certain embodiments, a humanized antibody comprises substantially all of at least one, and typically two, variable domains, in which all or substantially all of the CDRs correspond to those of a non-human immunoglobulin and all or substantially all of the framework regions are those of a human immunoglobulin consensus sequence. For the purposes of the present disclosure, humanized antibodies can also include immunoglobulin fragments, such as Fv, Fab, Fab', F(ab')$_2$ or other antigen-binding subsequences of antibodies.

The humanized antibody can also comprise at least a portion of an immunoglobulin constant region (Fc), typically that of a human immunoglobulin. See, for example, Jones et al. (1986) *Nature* 321:522-525; Riechmann et al. (1988) Nature 332:323-329; and Presta (1992) *Curr. Op. Struct. Biol.* 2:593-596.

Methods for humanizing non-human antibodies are known in the art. Generally, a humanized antibody has one or more amino acid residues introduced into it from a source that is non-human. These non-human amino acid residues are often referred to as "import" or "donor" residues, which are typically obtained from an "import" or "donor" variable domain. For example, humanization can be performed essentially according to the method of Winter and co-workers, by substituting rodent CDRs or CDR sequences for the corresponding sequences of a human antibody. See, for example, Jones et al., supra; Riechmann et al., supra and Verhoeyen et al. (1988) Science 239:1534-1536. Accordingly, such "humanized"

antibodies include chimeric antibodies (U.S. Pat. No. 4,816,567), wherein substantially less than an intact human variable domain has been substituted by the corresponding sequence from a non-human species. In certain embodiments, humanized antibodies are human antibodies in which some CDR residues and optionally some framework region residues are substituted by residues from analogous sites in rodent antibodies (e.g., murine monoclonal antibodies).

Human antibodies can also be produced, for example, by using phage display libraries. Hoogenboom et al. (1991) *J. Mol. Biol,* 227:381; Marks et al. (1991) *J. Mol. Biol.* 222:581. Other methods for preparing human monoclonal antibodies are described by Cole et al. (1985) "Monoclonal Antibodies and Cancer Therapy," Alan R. Liss, p. 77 and Boerner et al. (1991) *J. Immunol.* 147:86-95.

Human antibodies can be made by introducing human immunoglobulin loci into transgenic animals (e.g., mice) in which the endogenous immunoglobulin genes have been partially or completely inactivated. Upon immunological challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. (1992) *Bio/Technology* 10:779-783 (1992); Lonberg et al. (1994) *Nature* 368: 856-859; Morrison (1994) *Nature* 368: 812-813; Fishwald et al. (1996) *Nature Biotechnology* 14:845-851; Neuberger (1996) *Nature Biotechnology* 14:826; and Lonberg et al. (1995) *Intern. Rev. Immunol.* 13:65-93.

Antibodies can be affinity matured using known selection and/or mutagenesis methods as described above. In some embodiments, affinity matured antibodies have an affinity which is five times or more, ten times or more, twenty times or more, or thirty times or more than that of the starting antibody (generally murine, rabbit, chicken, humanized or human) from which the matured antibody is prepared.

An antibody can also be a bispecific antibody. Bispecific antibodies are monoclonal, and may be human or humanized antibodies that have binding specificities for at least two different antigens. In the present case, the two different binding specificities can be directed to two different MMPs, or to two different epitopes on a single MMP (e.g., MMP9).

An antibody as disclosed herein can also be an immunoconjugate. Such immunoconjugates comprise an antibody (e.g., to MMP9) conjugated to a second molecule, such as a reporter An immunoconjugate can also comprise an antibody conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

An antibody that "specifically binds to" or is "specific for" a particular polypeptide or an epitope on a particular polypeptide is one that binds to that particular polypeptide or epitope without substantially binding to any other polypeptide or polypeptide epitope. In some embodiments, an antibody of the present disclosure specifically binds to human MMP9 with a dissociation constant ($K_d$) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM; in the form of monoclonal antibody, scFv, Fab, or other form of antibody measured at a temperature of about 4° C., 25° C., 37° C. or 42° C.

In certain embodiments, an antibody of the present disclosure binds to one or more processing sites (e.g., sites of proteolytic cleavage) in MMP9, thereby effectively blocking processing of the proenzyme or preproenzyme to the catalytically active enzyme, and thus reducing the proteolytic activity of the MMP9.

In certain embodiments, an antibody according to the present disclosure binds to MMP9 with an affinity at least 2 times, at least 5 times, at least 10 times, at least 25 times, at least 50 times, at least 100 times, at least 500 times, or at least 1000 times greater than its binding affinity for another MMP. Binding affinity can be measured by any method known in the art and can be expressed as, for example, on-rate, off-rate, dissociation constant ($K_d$), equilibrium constant ($K_{eq}$) or any term in the art.

In certain embodiments, an antibody according to the present disclosure is a non-competitive inhibitor of the catalytic activity of MMP9. In certain embodiments, an antibody according to the present disclosure binds within the catalytic domain of MMP9. In additional embodiments, an antibody according to the present disclosure binds outside the catalytic domain of MMP9.

The present disclosure also contemplates antibodies or antigen binding fragments thereof, that compete with anti-MMP9 antibodies or antigen binding fragments thereof described herein for binding to MMP9. Thus, the present disclosure contemplates anti-MMP9 antibodies, and functional fragments thereof, that compete for binding with, for example, an antibody having a heavy chain polypeptide of any of SEQ ID NOS; 1 or 5-8, a light chain polypeptide of SEQ ID NOS:2 or 9-12, or combinations thereof. In one embodiment, the anti-MMP9 antibody, for functional fragment thereof, competes for binding to human MMP9 with the antibody described herein as AB0041.

MMP9 Sequence

The amino acid sequence of human MMP9 protein is as follows:

```
                                                          (SEQ ID NO: 27)
        MSLWQPLVLV  LLVLGCCFAA  PRQRQSTLVL  FPGDLRTNLT  DRQLAEEYLY     50

RYGYTRVAEM  RGESKSLGPA  LLLLQKQLSL  PETGELDSAT  LKAMRTPRCG    100

VPDLGRFQTF  EGDLKWHHHN  ITYWIQNYSE  DLPRAVIDDA  FARAFALWSA    150

VTPLTFTRVY  SRDADIVIQF  GVAEHGDGYP  FDGKDGLLAH  AFPPGPGIQG    200

DAHFDDDELW  SLGKGVVVPT  RFGNADGAAC  HFPFIFEGRS  YSACTTDGRS    250

DGLPWCSTTA  NYDTDDRFGF  CPSERLYTRD  GNADGKPCQF  PFIFQGQSYS    300

ACTTDGRSDG  YRWCATTANY  DRDKLFGFCP  TRADSTVMGG  NSAGELCVFP    350
```

```
FTFLGKEYST CTSEGRGDGR LWCATTSNFD SDKKWGFCPD QGYSLFLVAA    400

HEFGHALGLD HSSVPEALMY PMYRFTEGPP LHKDDVNGIR HLYGPRPEPE    450

PRPPTTTTPQ PTAPPTVCPT GPPTVHPSER PTAGPTGPPS AGPTGPPTAG    500

PSTATTVPLS PVDDACNVNI FDAIAEIGNQ LYLFKDGKYW RFSEGRGSRP    550

QGPFLIADKW PALPRKLDSV FEEPLSKKLF FFSGRQVWVY TGASVLGPRR    600

LDKLGLGADV AQVTGALRSG RGKMLLFSGR RLWRFDVKAQ MVDPRSASEV    650

DRMFPGVPLD THDVFQYREK AYFCQDRFYW RVSSRSELNQ VDQVGYVTYD    700

ILQCPED
```

Protein domains are shown schematically in FIG. 3 and are indicated below:

| Amino Acid # | Feature |
|---|---|
| 1-19 | Signal Peptide |
| 38-98 | Peptidoglycan Binding Domain |
| R98/C99 | Propetide cleavage site (dependent on cleavage enzyme) |
| 112-445 | Zn dependent metalloproteinase domain |
| 223-271 | Fibronectin type II domain (gelatin binding domain) |
| 281-329 | Fibronectin type II domain (gelatin binding domain) |
| 340-388 | Fibronectin type II domain (gelatin binding domain) |
| 400-411 | Zn binding region |
| 521-565 | Hemopexin-like domain |
| 567-608 | Hemopexin-like domain |
| 613-659 | Hemopexin-like domain |
| 661-704 | Hemopexin-like domain |

The amino acid sequence of mature full-length human MMP9 (which is the amino acid sequence of the propolypeptide of SEQ ID NO:27 without the signal peptide) is:

```
                                           (SEQ ID NO: 28)
PRQRQSTLVL FPGDLRTNLT DRQLAEEYLY RYGYTRVAEM

RGESKSLGPA LLLLQKQLSL PETGELDSAT LKAMRTPRCG

VPDLGRFQTF EGDLKWHHHN ITYWIQNYSE DLPRAVIDDA

FARAFALWSA VTPLTFTRVY SRDADIVIQF GVAEHGDGYP

FDGKDGLLAH AFPPGPGIQG DAHFDDDELW SLGKGVVVPT

RFGNADGAAC HFPFIFEGRS YSACTTDGRS DGLPWCSTTA

NYDTDDRFGF CPSERLYTRD GNADGKPCQF PFIFQGQSYS

ACTTDGRSDG YRWCATTANY DRDKLFGFCP TRADSTVMGG

NSAGELCVFP FTFLGKEYST CTSEGRDGR LWCATTSNFD

SDKKWGFCPD QGYSLFLVAA HEFGHALGLD HSSVPEALMY

PMYRFTEGPP LHKDDVNGIR HLYGPRPEPE PRPPTTTTPQ

PTAPPTVCPT GPPTVHPSER PTAGPTGPPS AGPTGPPTAG

PSTATTVPLS PVDDACNVNI FDAIAEIGNQ LYLFKDGKYW

RFSEGRGSRP QGPFLIADKW PALPRKLDSV FEEPLSKKLF

FFSGRQVWVY TGASVLGPRR LDKLGLGADV AQVTGALRSG

RGKMLLFSGR RLWRFDVKAQ MVDPRSASEV DRMFPGVPLD

THDVFQYREK AYFCQDRFYW RVSSRSELNQ VDQVGYVTYD

ILQCPED
``` where the amino acid sequence of the signal peptide is MSLWQPLVLV LLVLGCCFAA (SEQ ID NO:29).

The present disclosure contemplate MMP9 binding proteins that bind any portion of MMP9, e.g., human MMP9, with MMP9 binding proteins that preferentially bind MMP9 relative to other MMPs being of particular interest.

Anti-MMP9 antibodies, and functional fragments thereof, can be generated accordingly to methods well known in the art. Examples of anti-MMP9 antibodies are provided below.

Mouse Monoclonal Anti-MMP9

A mouse monoclonal antibody to human MMP9 was obtained as described in Example 1. This antibody contains a mouse IgG2b heavy chain and a mouse kappa light chain, and is denoted AB0041.

The amino acid sequence of the AB0041 heavy chain is as follows:

```
                                            (SEQ ID NO: 1)
MAVLVLFLCLVAFPSCVLSQVQLKESGPGLVAPSQSLSITCTVSGFSLL

SYGVHWVRQPPGKGLEWLGVIWTGGTTNYNSALMSRLSISKDDSKSQVF

LKMNSLQTDDTAIYYCARYYYGMDYWGQGTSVTVSSAKTTPPSVYPLAP

GCGDTTGSSVTLGCLVKGYFPESVTVTWNSGSLSSSVHTFPALLQSGLY

TMSSSVTVPSSTWPSQTVTCSVAHPASSTTVDKKLEPSGPISTINPCPP

CKECHKCPAPNLEGGPSVFIFPPNIKDVLMISLTPKVTCVVVDVSEDDP

DVRISWFVNNVEVHTAQTQTHREDYNSTIRVVSALPIQHQDWMSGKEFK

CKVNNKDLPSPIERTISKIKGLVRAPQVYILPPPAEQLSRKDVSLTCLV

VGFNPGDISVEWTSNGHTEENYKDTAPVLDSDGSYFIYSKLDIKTSKWE

KTDSFSCNVRHEGLKNYYLKKTISRSPGK
```

The signal sequence is underlined, and the sequence of the IgG2b constant region is presented italics.

The amino acid sequence of the AB0041 light chain is as follows:

```
                                            (SEQ ID NO: 2)
MESQIQVFVFVFLWLSGVDGDIVMTQSHKFMSTSVGDRVSITCKASQDV

RNTVAWYQQKTGQSPKLLIYSSSYRNTGVPDRFTGSGSGTDFTFTISSV

QAEDLAVYFCQQHYITPYTFGGGTKLEIKRADAAPTVSIFPPSSEQLTS

GGASVVCFLNNFYPKDINVKWKIDGSERQNGVLNSWTDQDSKDSTYSMS

STLTLTKDEYERHNSYTCEATHKTSTSPIVKSFNRNEC
```

The signal sequence is underlined, and the sequence of the kappa constant region is presented in italics.

The following amino acid sequence comprises the framework regions and complementarity-determining regions (CDRs) of the variable region of the IgG2b heavy chain of AB0041 (with CDRs underlined):

(SEQ ID NO: 3)
QVQLKESGPGLVAPSQSLSITCTVS<u>GFSLLSYGVH</u>WVRQPPGKGLEWLG

<u>VIWTGGTTNYNSALMSR</u>LSISKDDSKSQVFLKMNSLQTDDTAIYYCAR<u>Y</u>

<u>YYGMDY</u>WGQGTSVTVSS

The following amino acid sequence comprises the framework regions and complementarity-determining regions (CDRs) of the variable region of the kappa light chain of AB0041 (with CDRs underlined):

(SEQ ID NO: 4)
DIVMTQSHKFMSTSVGDRVSITC<u>KASQDVRNTV</u>AWYQQKTGQSPKLLIY

<u>SSSYRNT</u>GVPDRFTGSGSGTDFTFTISSVQAEDLAVYFC<u>QQHYITPYTF</u>

GGGTKLEIK

Heavy-Chain Variants

The amino acid sequences of the variable regions of the AB0041 heavy and light chains were separately modified, by altering framework region sequences in the heavy and light chain variable regions. The effect of these sequence alterations was to deplete the antibody of human T-cell epitopes, thereby reducing or abolishing its immunogenicity in humans (Antitope, Babraham, UK).

Four heavy-chain variants were constructed, in a human IgG4 heavy chain background containing a S241P amino acid change that stabilizes the hinge domain (Angal et al. (1993) Molec. Immunol. 30:105-108), and are denoted VH1, VH2, VH3 and VH4. The amino acid sequences of their framework regions and CDRs are as follows:

VH1
(SEQ ID NO: 5)
QVQLQESGPGLVKPSETLSLTCTVSGFSLLSYGVHWVRQPPGKGLEWLG

VIWTGGTTNYNSALMSRLTISKDDSKSTVYLKMNSLKTEDTAIYYCARY

YYGMDYWGQGTSVTVSS

VH2
(SEQ ID NO: 6)
QVQLQESGPGLVKPSETLSLTCTVSGFSLLSYGVHWVRQPPGKGLEWLG

VIWTGGTTNYNSALMSRLTISKDDSKNTVYLKMNSLKTEDTAIYYCARY

YYGMDYWGQGTLVTVSS

VH3
(SEQ ID NO: 7)
QVQLQESGPGLVKPSETLSLTCTVSGFSLLSYGVHWVRQPPGKGLEWLG

VIWTGGTTNYNSALMSRFTISKDDSKNTVYLKMNSLKTEDTAIYYCARY

YYGMDYWGQGTLVTVSS

VH4
(SEQ ID NO: 8)
QVQLQESGPGLVKPSETLSLTCTVSGFSLLSYGVHWVRQPPGKGLEWLG

VIWTGGTTNYNSALMSRFTISKDDSKNTLYLKMNSLKTEDTAIYYCARY

YYGMDYWGQGTLVTVSS

FIG. 1 shows an alignment of the amino acid sequences of the variable regions of the humanized heavy chains and indicates the differences in amino acid sequences in the framework regions among the four variants.

Light-Chain Variants

Four light-chain variants were constructed, in a human kappa chain background, and are denoted Vk1, Vk2, Vk3 and Vk4. The amino acid sequences of their framework regions and CDRs are as follows:

Vk1
(SEQ ID NO: 9)
DIVMTQSPSFLSASVGDRVTITCKASQDVRNTVAWYQQKTGKAPKLLIY

SSSYRNTGVPDRFTGSGSGTDFTLTISSLQAEDVAVYFCQQHYITPYTF

GGGTKVEIK

Vk2
(SEQ ID NO: 10)
DIVMTQSPSSLSASVGDRVTITCKASQDVRNTVAWYQQKPGKAPKLLIY

SSSYRNTGVPDRFTGSGSGTDFTLTISSLQAEDVAVYFCQQHYITPYTF

GGGTKVEIK

Vk3
(SEQ ID NO: 11)
DIQMTQSPSSLSASVGDRVTITCKASQDVRNTVAWYQQKPGKAPKLLIY

SSSYRNTGVPDRFSGSGSGTDFTLTISSLQAEDVAVYFCQQHYITPYTF

GGGTKVEIK

Vk4
(SEQ ID NO: 12)
DIQMTQSPSSLSASVGDRVTITCKASQDVRNTVAWYQQKPGKAPKLLIY

SSSYRNTGVPDRFSGSGSGTDFTLTISSLQAEDVAVYYCQQHYITPYTF

GGGTKVEIK

FIG. 2 shows an alignment of the amino acid sequences of the variable regions of the humanized light chains and indicates the differences in amino acid sequences in the framework regions among the four variants.

The humanized heavy and light chains are combined in all possible pair-wise combinations to generate a number of functional humanized anti-MMP9 antibodies.

Additional heavy chain variable region amino acid sequences having 75% or more, 80% or more, 90% or more, 95% or more, or 99% or more homology to the heavy chain variable region sequences disclosed herein are also provided. Furthermore, additional light chain variable region amino acid sequences having 75% or more, 80% or more, 90% or more, 95% or more, or 99% or more homology to the light chain variable region sequences disclosed herein are also provided.

Additional heavy chain variable region amino acid sequences having 75% or more, 80% or more, 90% or more, 95% or more, or 99% or more sequence identity to the heavy chain variable region sequences disclosed herein are also provided. Furthermore, additional light chain variable region amino acid sequences having 75% or more, 80% or more, 90% or more, 95% or more, or 99% or more sequence identity to the light chain variable region sequences disclosed herein are also provided.

Complementarity-Determining Regions (CDRs)

The CDRs of the heavy chain of an anti-MMP9 antibody as disclosed herein have the following amino acid sequences:

CDR1:
(SEQ ID NO: 13)
GFSLLSYGVH

CDR2:
(SEQ ID NO: 14)

```
-continued
VIWTGGTTNYNSALMS

CDR3:
                                          (SEQ ID NO: 15)
YYYGMDY
```

The CDRs of the light chain of an anti-MMP9 antibody as disclosed herein have the following amino acid sequences:

```
CDR1:
                                          (SEQ ID NO: 16)
KASQDVRNTVA

CDR2:
                                          (SEQ ID NO: 17)
SSSYRNT

CDR3:
                                          (SEQ ID NO: 18)
QQHYITPYT
```

Nucleic Acids Encoding Anti-MMP9 Antibodies

The present disclosure provides nucleic acids encoding anti-MMP9 antibodies and functional fragments thereof. Accordingly, the present disclosure provides an isolated polynucleotide (nucleic acid) encoding an antibody or antigen-binding fragment as described herein, vectors containing such polynucleotides, and host cells and expression systems for transcribing and translating such polynucleotides into polypeptides.

The present disclosure also contemplates constructs in the form of plasmids, vectors, transcription or expression cassettes which comprise at least one polynucleotide as above.

The present disclosure also provides a recombinant host cell which comprises one or more constructs as above, as well as methods of production of the antibody or antigen-binding fragments thereof described herein which method comprises expression of nucleic acid encoding a heavy chain polypeptide and a light chain polypeptide (in the same or different host cells, and from the same or different constructs) in a recombination host cell. Expression can be achieved by culturing under appropriate conditions recombinant host cells containing the nucleic acid. Following production by expression, an antibody or antigen-binding fragment can be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is *E. coli.*

Suitable vectors can be chosen or constructed, containing appropriate regulatory sequences, including operably linked promoter sequences, terminator sequences, polyadenylation sequences, enhancer sequences, marker genes and/or other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference in their entirety.

The nucleic acid encoding a polypeptide of interest is integrated into the genome of the host cell or can be maintained as a stable or transient episomal element.

Any of a wide variety of expression control sequences—sequences that control the expression of a DNA sequence operatively linked to it—can be used in these vectors to express the DNA sequences. For example, a nucleic acid encoding a polypeptide of interest can be operably linked to a promoter, and provided in an expression construct for use in methods of production of recombinant MMP9 proteins or portions thereof.

Those of skill in the art are aware that nucleic acids encoding the antibody chains disclosed herein can be synthesized using standard knowledge and procedures in molecular biology.

Examples of nucleotide sequences encoding the heavy and light chain amino acid sequences disclosed herein, are as follows:

```
VH1:
                                          (SEQ ID NO: 19)
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGGAAGG GCCTGGAATG GCTGGGCGTG ATCTGGACCG

GCGGCACCAC CAACTACAAC TCCGCCCTGA TGTCCCGGCT

GACCATCTCC AAGGACGACT CCAAGTCCAC CGTGTACCTG

AAGATGAACT CCCTGAAAAC CGAGGACACC GCCATCTACT

ACTGCGCCCG GTACTACTAC GGCATGGACT ACTGGGGCCA

GGGCACCTCC GTGACCGTGT CCTCA

VH2:
                                          (SEQ ID NO: 20)
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGCAAAG GCCTGGAATG GCTGGGCGTG ATCTGGACCG

GCGGCACCAC CAACTACAAC TCCGCCCTGA TGTCCCGGCT

GACCATCTCC AAGGACGACT CCAAGAACAC CGTGTACCTG

AAGATGAACT CCCTGAAAAC CGAGGACACC GCCATCTACT

ACTGCGCCCG GTACTACTAC GGCATGGACT ACTGGGGCCA

GGGCACCCTG GTCACCGTGT CCTCA

VH3:
                                          (SEQ ID NO: 21)
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGCAAAG GCCTGGAATG GCTGGGCGTG ATCTGGACCG

GCGGCACCAC CAACTACAAC TCCGCCCTGA TGTCCCGGTT

CACCATCTCC AAGGACGACT CCAAGAACAC CGTGTACCTG

AAGATGAACT CCCTGAAAAC CGAGGACACC GCCATCTACT
```

```
ACTGCGCCCG GTACTACTAC GGCATGGACT ACTGGGGCCA

GGGCACCCTG GTCACCGTGT CCTCA
```

VH4:
(SEQ ID NO: 22)
```
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGCAAAG GCCTGGAATG GCTGGGCGTG ATCTGGACCG

GCGGCACCAC CAACTACAAC TCCGCCCTGA TGTCCGGTT

CACCATCTCC AAGGACGACT CCAAGAACAC CCTGTACCTG

AAGATGAACT CCCTGAAAAC CGAGGACACC GCCATCTACT

ACTGCGCCCG GTACTACTAC GGCATGGACT ACTGGGGCCA

GGGCACCCTG GTCACCGTGT CCTCA
```

Vk1:
(SEQ ID NO: 23)
```
GACATCGTGA TGACCCAGTC CCCCAGCTTC CTGTCCGCCT

CCGTGGGCGA CAGAGTGACC ATCACATGCA AGGCCTCTCA

GGACGTGCGG AACACCGTGG CCTGGTATCA GCAGAAAACC

GGCAAGGCCC CCAAGCTGCT GATCTACTCC TCCTCCTACC

GGAACACCGG CGTGCCCGAC CGGTTTACCG GCTCTGGCTC

CGGCACCGAC TTTACCCTGA CCATCAGCTC CCTGCAGGCC

GAGGACGTGG CCGTGTACTT CTGCCAGCAG CACTACATCA

CCCCCTACAC CTTCGGCGGA GGCACCAAGG TGGAAATAAA A
```

Vk2:
(SEQ ID NO: 24)
```
GACATCGTGA TGACCCAGTC CCCCTCCAGC CTGTCCGCCT

CTGTGGGCGA CAGAGTGACC ATCACATGCA AGGCCTCTCA

GGACGTGCGG AACACCGTGG CCTGGTATCA GCAGAAGCCC

GGCAAGGCCC CCAAGCTGCT GATCTACTCC TCCTCCTACC

GGAACACCGG CGTGCCCGAC CGGTTTACCG GCTCTGGCTC

CGGCACCGAC TTTACCCTGA CCATCAGCTC CCTGCAGGCC

GAGGACGTGG CCGTGTACTT CTGCCAGCAG CACTACATCA

CCCCCTACAC CTTCGGCGGA GGCACCAAGG TGGAAATAAA A
```

Vk3:
(SEQ ID NO: 25)
```
GACATCCAGA TGACCCAGTC CCCCTCCAGC CTGTCCGCCT

CTGTGGGCGA CAGAGTGACC ATCACATGCA AGGCCTCCCA

GGACGTGCGG AACACCGTGG CCTGGTATCA GCAGAAGCCC

GGCAAGGCCC CCAAGCTGCT GATCTACTCC TCCTCCTACC

GGAACACCGG CGTGCCCGAC CGGTTCTCTG GCTCTGGAAG

CGGCACCGAC TTTACCCTGA CCATCAGCTC CCTGCAGGCC

GAGGACGTGG CCGTGTACTT CTGCCAGCAG CACTACATCA

CCCCCTACAC CTTCGGCGGA GGCACCAAGG TGGAAATAAA A
```

Vk4:
(SEQ ID NO: 26)
```
GACATCCAGA TGACCCAGTC CCCCTCCAGC CTGTCCGCCT

CTGTGGGCGA CAGAGTGACC ATCACATGCA AGGCCTCTCA

GGACGTGCGG AACACCGTGG CCTGGTATCA GCAGAAGCCC

GGCAAGGCCC CCAAGCTGCT GATCTACTCC TCCTCCTACC

GGAACACCGG CGTGCCCGAC CGGTTCTCTG GCTCTGGAAG

CGGCACCGAC TTTACCCTGA CCATCAGCTC CCTGCAGGCC

GAGGACGTGG CCGTGTACTA CTGCCAGCAG CACTACATCA

CCCCCTACAC CTTCGGCGGA GGCACCAAGG TGGAAATAAA A
```

Because the structure of antibodies, including the juxtaposition of CDRs and framework regions in the variable region, the structure of framework regions and the structure of heavy- and light-chain constant regions, is well-known in the art; it is well within the skill of the art to obtain related nucleic acids that encode anti-MMP-9 antibodies. Accordingly, polynucleotides comprising nucleic acid sequences having at least 75%, at least 80%, at least 85%, at least 90%, at least 95%, at least 98% and at least 99% homology to any of the nucleotide sequences disclosed herein are also provided. Accordingly, polynucleotides comprising nucleic acid sequences having at least 75%, at least 80%, at least 85%, at least 90%, at least 95%, at least 98% and at least 99% identity to any of the nucleotide sequences disclosed herein are also provided.

Pharmaceutical Compositions

MMP9 binding proteins, as well as nucleic acid (e.g., DNA or RNA) encoding MMP9 binding proteins, can be provided as a pharmaceutical composition, e.g., combined with a pharmaceutically acceptable carrier or excipient. Such pharmaceutical compositions are useful for, for example, administration to a subject in vivo or ex vivo, and for diagnosing and/or treating a subject with the MMP9 binding proteins.

Pharmaceutically acceptable carriers are physiologically acceptable to the administered patient and retain the therapeutic properties of the antibodies or peptides with which it is administered. Pharmaceutically-acceptable carriers and their formulations are and generally described in, for example, Remington' pharmaceutical Sciences (18th Edition, ed. A. Gennaro, Mack Publishing Co., Easton, Pa. 1990). One exemplary pharmaceutical carrier is physiological saline. Each carrier is "pharmaceutically acceptable" in the sense of being compatible with the other ingredients of the formulation and not substantially injurious to the patient.

Pharmaceutical compositions can be formulated to be compatible with a particular route of administration, systemic or local. Thus, pharmaceutical compositions include carriers, diluents, or excipients suitable for administration by various routes.

Pharmaceutical compositions can include pharmaceutically acceptable additives. Examples of additives include, but are not limited to, a sugar such as mannitol, sorbitol, glucose, xylitol, trehalose, sorbose, sucrose, galactose, dextran, dextrose, fructose, lactose and mixtures thereof. Pharmaceutically acceptable additives can be combined with pharmaceutically acceptable carriers and/or excipients such as dextrose. Additives also include surfactants such as polysorbate 20 or polysorbate 80.

The formulation and delivery methods will generally be adapted according to the site and the disease to be treated. Exemplary formulations include, but are not limited to, those suitable for parenteral administration, e.g., intravenous, intraarterial, intramuscular, or subcutaneous administration.

Pharmaceutical compositions for parenteral delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65 75; Warren (1997) J. Neurol. Sci. 152:31 38; and Tonegawa (1997) J. Exp. Med. 186:507 515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

Compositions of the present invention can be combined with other therapeutic moieties or imaging/diagnostic moieties as provided herein. Therapeutic moieties and/or imaging moieties can be provided as a separate composition, or as a conjugated moiety present on an MMP9 binding protein.

Formulations for in vivo administration are generally sterile. In one embodiment, the pharmaceutical compositions are formulated to be free of pyrogens such that they are acceptable for administration to human patients.

Various other pharmaceutical compositions and techniques for their preparation and use will be known to those of skill in the art in light of the present disclosure. For a detailed listing of suitable pharmacological compositions and associated administrative techniques one can refer to the detailed teachings herein, which can be further supplemented by texts such as Remington: The Science and Practice of Pharmacy 20th Ed. (Lippincott, Williams & Wilkins 2003).

Pharmaceutical compositions can be formulated based on the physical characteristics of the patient/subject needing treatment, the route of administration, and the like. Such can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages and kits described below.

Methods of Use

The MMP9 binding proteins of the present disclosure can be used in, for example, methods of detection of MMP9 in a sample, methods of treatment (e.g., as in methods of inhibition of angiogenesis), and methods of diagnosis. Examples of methods of use are described below.

Methods of Treatment

Provided herein are methods of treating diseases and disorders associated with MMP9 activity. Diseases and disorder include, but are not limited to tumors (e.g., primary or metastatic) that express or are disposed in a tissue which expresses MMP9.

As used herein, "treat" or "treatment" means stasis or a postponement of development of the symptoms associated a disease or disorder described herein. The terms further include ameliorating existing uncontrolled or unwanted symptoms, preventing additional symptoms, and ameliorating or preventing the underlying metabolic causes of symptoms. Thus, the terms denote that a beneficial result has been conferred on a mammalian subject with a disease or symptom, or with the potential to develop such disease or symptom. A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors.

The present disclosure contemplates pharmaceutical compositions for use in connection with such methods. Compositions can be suitable for administration locally or systemically by any suitable route.

In general, MMP9 binding proteins are administered in a therapeutically effective amount, e.g., in an amount to effect inhibition of tumor growth in a subject and/or to inhibit metastasis.

As used herein, the term "therapeutically effective amount" or "effective amount" refers to an amount of a therapeutic agent that when administered alone or in combination with another therapeutic agent to a subject is effective to prevent or ameliorate the disease condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. For example, when in vivo administration of an anti-MMP9 antibody is employed, normal dosage amounts can vary from about 10 ng/kg to up to 100 mg/kg of mammal body weight or more per day, preferably about 1 µg/kg/day to 50 mg/kg/day, optionally about 100 µg/kg/day to 20 mg/kg/day, 500 µg/kg/day to 10 mg/kg/day, or 1 mg/kg/day to 10 mg/kg/day, depending upon the route of administration.

The selected dosage regimen will depend upon a variety of factors including the activity of the MMP9 binding protein, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

A clinician having ordinary skill in the art can readily determine and prescribe the effective amount (ED50) of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved.

As used herein, the term "subject" means mammalian subjects. Exemplary subjects include, but are not limited to humans, monkeys, dogs, cats, mice, rats, cows, horses, goats and sheep. In some embodiments, the subject has cancer and can be treated with the agent of the present invention as described below.

If needed, for cancer treatments, methods can further include surgical removal of the cancer and/or administration of an anti-cancer agent or treatment in addition to an MMP9 binding protein. Administration of such an anti-cancer agent or treatment can be concurrent with administration of the compositions disclosed herein.

Methods of Detection of MMP9

The present disclosure also contemplates methods of detecting MMP9 in a subject, e.g., to detect tumor or tumor-associated tissue expressing MMP9. Thus, methods of diagnosing, monitoring, staging or detecting a tumor having MMP9 activity are provided.

Samples from an individual suspected of having a tumor associated with MMP9 expression can be collected and analyzed by detecting the presence or absence of binding of an MMP9 binding protein. This analysis can be performed prior to the initiation of treatment using an MMP9 binding protein as described herein, or can be done as part of monitoring of progress of cancer treatment. Such diagnostic analysis can be performed using any sample, including but not limited to tissue, cells isolated from such tissues, and the like. Tissue samples include, for example, formalin-fixed or frozen tissue sections.

Any suitable method for detection and analysis of MMP9 be employed. Various diagnostic assay techniques known in the art can be adapted for such purpose, such as competitive binding assays, direct or indirect sandwich assays and immunoprecipitation assays conducted in either heterogeneous or homogeneous phases.

MMP9 binding proteins for use in detection methods can be labeled with a detectable moiety. The detectable moiety directly or indirectly produces a detectable signal. For example, the detectable moiety can be any of those described herein such as, for example, a radioisotope, such as 3H, 14C, 32P, 35S, or 125I, a fluorescent or chemiluminescent compound, such as fluorescein isothiocyanate (FITC), Texas red, cyanin, photocyan, rhodamine, or luciferin, or an enzyme, such as alkaline phosphatase, β-galactosidase or horseradish peroxidase.

Detection can be accomplished by contacting a sample under conditions suitable for MMP9 binding protein binding to MMP9, and assessing the presence (e.g., level) or absence of MMP9 binding protein-MMP9 complexes. A level of MMP9 in the sample in comparison with a level of a reference sample can indicate the presence of a tumor or tumor-associated tissues having MMP9 activity. The reference sample can be a sample taken from the subject at an earlier time point or a sample from another individual.

EXAMPLES

Example 1

Preparation of Antibodies to Human MMP-9

The full-length human MMP9 protein without a signal peptide, which is SEQ ID NO. 28 was used to immunize mice. Spleen cells from immunized mice were fused with myeloma cells to generate a hybridoma library. Monoclonal cultures were prepared and screened to identify cultures expressing an anti-MMP9 monoclonal antibody.

Antibody (AB0041) was purified from one of the cultures and characterized. The antibody contained an IgG2b heavy chain and a kappa light chain. Characterization included testing for the binding of AB0041 to other human MMPs and to MMP9 proteins from other species, including cynomolgus monkey, rat and mouse. It was found that the AB0041 antibody bound strongly to human and cynomolgus MMP9, that it bound less strongly to rat MMP9, and that it did not bind to murine MMP9 or to many of the human non-MMP matrix metalloproteinases.

TABLE 2

Cross reactivity of AB0041 and AB0045.

| | Dissociation constant (Kd) | |
|---|---|---|
| MMP Tested | AB0045 | AB0041 |
| Human MMP1 | >100 nM | >100 nM |
| Human MMP2 | >100 nM | >100 nM |
| Mouse MMP2 | >100 nM | >100 nM |
| Human MMP3 | >100 nM | >100 nM |
| Human MMP7 | >100 nM | >100 nM |
| Human MMP8 | >100 nM | >100 nM |
| Human MMP9 | 0.168 ± 0.117 nM | 0.133 ± 0.030 nM |
| Cynomolgus monkey MMP9 | 0.082 ± 0.022 nM | 0.145 ± 0.16 nM |

TABLE 2-continued

Cross reactivity of AB0041 and AB0045.

| | Dissociation constant (Kd) | |
|---|---|---|
| MMP Tested | AB0045 | AB0041 |
| Mouse MMP9 | >100 nM | >100 nM |
| Rat MMP9 | 0.311 ± 0.017 nM | 0.332 ± 0.022 nM |
| Human MMP10 | >100 nM | >100 nM |
| Human MMP12 | >100 nM | >100 nM |
| Human MMP13 | >100 nM | >100 nM |

Additional characterization included assaying the binding of the antibody to mouse MMP9 in which certain amino acids were altered to more closely correspond to the human MMP9 sequence. In addition, the human MMP9 protein was mutagenized, and the various mutants tested for their ability to be bound by the antibody, to determine amino acids important for antibody binding and thereby define the therapeutic epitope. This analysis identified an arginine residue at position 162 of the MMP9 amino acid sequence (R162) as important for antibody binding. Other amino acid residues in MMP9 that are important for binding of the AB0041 antibody include E111, D113, and I198. Recent crystal structure of MMP9 showed that E111, D113, R162, and I198 were grouped near each other around a Ca2+ ion binding pocket of MMP9. Without binding to any specific scientific theory, AB0041 may bind to the region on MMP9 wherein these residues are located. Alternatively, these MMP9 residues may have direct contact with AB0041.

In an enzymatic assay for MMP9, the AB0041 antibody was found to act as a non-competitive inhibitor.

Example 2

Humanization of Antibodies to Human MMP9

The amino acid sequences of the heavy chain and light chain of the mouse AB0041 antibody were altered at certain locations in the framework (i.e., non-CDR) portion of their variable regions to generate proteins that are less immunogenic in humans. These amino acid sequence changes were shown in FIGS. 1 and 2. The cross-reactivity of the humanized antibody (referred to as AB0045) is shown in Table 2 above.

What is claimed is:

1. An isolated matrix metalloproteinase 9 (MMP9) binding protein, comprising
    an immunoglobulin heavy chain polypeptide, or functional fragment thereof, and
    an immunoglobulin light chain polypeptide, or functional fragment thereof,
    wherein the MMP9 binding protein specifically binds to human MMP9 and
    wherein the MMP9 binding protein competes for binding to human MMP9 with an antibody comprising heavy chain CDRs of SEQ ID NOs: 13-15 or light chain CDRs of SEQ ID NOs: 16-18.

2. The MMP9 binding protein of claim 1, wherein the antibody comprises complementarity-determining regions (CDRs) of SEQ ID NOs: 13-15 and light chain CDRs of SEQ ID NOs: 16-18.

3. The MMP9 binding protein of claim 1, wherein the immunoglobulin heavy chain polypeptide or functional fragment thereof comprises CDRs of SEQ ID NOs: 13-15, and the immunoglobulin light chain polypeptide comprises CDRs of SEQ ID NOs: 16-18.

4. The MMP9 binding protein of claim 1, wherein the immunoglobulin heavy chain polypeptide or functional fragment thereof comprises an amino acid sequence selected from the group consisting of SEQ ID NOs: 3 and 5-8.

5. The MMP9 binding protein of claim 1, wherein the immunoglobulin light chain polypeptide or functional fragment thereof comprises an amino acid sequence selected from the group consisting of SEQ ID NOs: 4 and 9-12.

6. The MMP9 binding protein of claim 1, wherein the immunoglobulin heavy chain polypeptide comprises the amino acid sequence of SEQ ID NO: 7 and the light chain comprises the amino acid sequence of SEQ ID NO: 12.

7. A pharmaceutical composition comprising the MMP9 binding protein of claim 1 and a pharmaceutically acceptable carrier.

* * * * *

SEQUENCE LISTING

```
<160> NUMBER OF SEQ ID NOS: 29

<210> SEQ ID NO 1
<211> LENGTH: 470
<212> TYPE: PRT
<213> ORGANISM: Mus musculus
<220> FEATURE:
<221> NAME/KEY: CHAIN
<222> LOCATION: (1)...(470)
<223> OTHER INFORMATION: AB0041 heavy chain
<220> FEATURE:
<221> NAME/KEY: PEPTIDE
<222> LOCATION: (1)...(19)
<223> OTHER INFORMATION: signal peptide
<220> FEATURE:
<221> NAME/KEY: misc_feature
<222> LOCATION: (135)...(470)
<223> OTHER INFORMATION: IgG2b constant region

<400> SEQUENCE: 1

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Leu Ser Ile Ser Lys Asp Asp Ser Lys Ser Gln
                85                  90                  95

Val Phe Leu Lys Met Asn Ser Leu Gln Thr Asp Asp Thr Ala Ile Tyr
            100                 105                 110

Tyr Cys Ala Arg Tyr Tyr Gly Met Asp Tyr Trp Gly Gln Gly Thr
        115                 120                 125

Ser Val Thr Val Ser Ser Ala Lys Thr Thr Pro Pro Ser Val Tyr Pro
    130                 135                 140
```

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
            195                 200                 205

Trp Pro Ser Gln Thr Val Thr Cys Ser Val Ala His Pro Ala Ser Ser
    210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
            260                 265                 270

Val Leu Met Ile Ser Leu Thr Pro Lys Val Thr Cys Val Val Val Asp
            275                 280                 285

Val Ser Glu Asp Asp Pro Asp Val Arg Ile Ser Trp Phe Val Asn Asn
290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ser Pro Ile Glu Arg Thr Ile Ser Lys Ile Lys Gly Leu Val Arg Ala
            355                 360                 365

Pro Gln Val Tyr Ile Leu Pro Pro Pro Ala Glu Gln Leu Ser Arg Lys
    370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
            420                 425                 430

Leu Asp Ile Lys Thr Ser Lys Trp Glu Lys Thr Asp Ser Phe Ser Cys
            435                 440                 445

Asn Val Arg His Glu Gly Leu Lys Asn Tyr Tyr Leu Lys Lys Thr Ile
    450                 455                 460

Ser Arg Ser Pro Gly Lys
465                 470

<210> SEQ ID NO 2
<211> LENGTH: 234
<212> TYPE: PRT
<213> ORGANISM: Mus musculus
<220> FEATURE:
<221> NAME/KEY: CHAIN
<222> LOCATION: (1)...(234)
<223> OTHER INFORMATION: AB0041 light chain
<220> FEATURE:
<221> NAME/KEY: PEPTIDE
<222> LOCATION: (1)...(20)
<223> OTHER INFORMATION: signal peptide
<220> FEATURE:
<221> NAME/KEY: misc_feature
<222> LOCATION: (128)...(234)
<223> OTHER INFORMATION: kappa constant region

```
<400> SEQUENCE: 2

Met Glu Ser Gln Ile Gln Val Phe Val Phe Val Leu Trp Leu Ser
 1               5                  10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Arg Asn Thr Val Ala Trp Tyr Gln Gln Lys Thr Gly Gln Ser Pro
    50                  55                  60

Lys Leu Leu Ile Tyr Ser Ser Ser Tyr Arg Asn Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Phe Cys Gln Gln His Tyr
            100                 105                 110

Ile Thr Pro Tyr Thr Phe Gly Gly Gly Thr Lys Leu Glu Ile Lys Arg
        115                 120                 125

Ala Asp Ala Ala Pro Thr Val Ser Ile Phe Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 3
<211> LENGTH: 115
<212> TYPE: PRT
<213> ORGANISM: Mus musculus
<220> FEATURE:
<221> NAME/KEY: CHAIN
<222> LOCATION: (1)...(115)
<223> OTHER INFORMATION: variable region of the IgG2b heavy chain of
      AB0041
<220> FEATURE:
<221> NAME/KEY: misc_feature
<222> LOCATION: (26)...(35)
<223> OTHER INFORMATION: complementarity-determining region (CDR)
<220> FEATURE:
<221> NAME/KEY: misc_feature
<222> LOCATION: (50)...(65)
<223> OTHER INFORMATION: complementarity-determining region (CDR)
<220> FEATURE:
<221> NAME/KEY: misc_feature
<222> LOCATION: (98)...(104)
<223> OTHER INFORMATION: complementarity-determining region (CDR)

<400> SEQUENCE: 3

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
```

```
                    35                  40                  45
Gly Val Ile Trp Thr Gly Thr Thr Asn Tyr Asn Ser Ala Leu Met
 50                  55                  60

Ser Arg Leu Ser Ile Ser Lys Asp Asp Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Arg Tyr Tyr Tyr Gly Met Asp Tyr Trp Gly Gln Gly Thr Ser Val Thr
                100                 105                 110

Val Ser Ser
        115

<210> SEQ ID NO 4
<211> LENGTH: 107
<212> TYPE: PRT
<213> ORGANISM: Mus musculus
<220> FEATURE:
<221> NAME/KEY: CHAIN
<222> LOCATION: (1)...(107)
<223> OTHER INFORMATION: variable region of the kappa light chain of
      AB0041
<220> FEATURE:
<221> NAME/KEY: misc_feature
<222> LOCATION: (24)...(34)
<223> OTHER INFORMATION: complementarity-determining region (CDR)
<220> FEATURE:
<221> NAME/KEY: misc_feature
<222> LOCATION: (50)...(56)
<223> OTHER INFORMATION: complementarity-determining region (CDR)
<220> FEATURE:
<221> NAME/KEY: misc_feature
<222> LOCATION: (89)...(97)
<223> OTHER INFORMATION: complementarity-determining region (CDR)

<400> SEQUENCE: 4

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Arg Asn Thr
                20                  25                  30

Val Ala Trp Tyr Gln Gln Lys Thr Gly Gln Ser Pro Lys Leu Leu Ile
             35                  40                  45

Tyr Ser Ser Ser Tyr Arg Asn Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Phe Cys Gln Gln His Tyr Ile Thr Pro Tyr
                 85                  90                  95

Thr Phe Gly Gly Gly Thr Lys Leu Glu Ile Lys
                100                 105

<210> SEQ ID NO 5
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH1 heavy chain variant

<400> SEQUENCE: 5

Gln Val Gln Leu Gln Glu Ser Gly Pro Gly Leu Val Lys Pro Ser Glu
 1               5                  10                  15
```

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
            35                  40                  45

Gly Val Ile Trp Thr Gly Gly Thr Thr Asn Tyr Asn Ser Ala Leu Met
 50                      55                  60

Ser Arg Leu Thr Ile Ser Lys Asp Asp Ser Lys Ser Thr Val Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Ser Val Thr
                100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH2 heavy chain variant

<400> SEQUENCE: 6

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
            35                  40                  45

Gly Val Ile Trp Thr Gly Gly Thr Thr Asn Tyr Asn Ser Ala Leu Met
 50                      55                  60

Ser Arg Leu Thr Ile Ser Lys Asp Asp Ser Lys Asn Thr Val Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Leu Val Thr
                100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH3 heavy chain variant

<400> SEQUENCE: 7

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu

-continued

```
                35                  40                  45
Gly Val Ile Trp Thr Gly Gly Thr Thr Asn Tyr Asn Ser Ala Leu Met
             50                  55                  60

Ser Arg Phe Thr Ile Ser Lys Asp Asp Ser Lys Asn Thr Val Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH4 heavy chain variant

<400> SEQUENCE: 8

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Leu Ser Tyr
             20                  25                  30

Gly Val His Trp Val Arg Gln Pro Pro Gly Lys Gly Leu Glu Trp Leu
             35                  40                  45

Gly Val Ile Trp Thr Gly Gly Thr Thr Asn Tyr Asn Ser Ala Leu Met
             50                  55                  60

Ser Arg Phe Thr Ile Ser Lys Asp Asp Ser Lys Asn Thr Leu Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk1 light chain variant

<400> SEQUENCE: 9

Asp Ile Val Met Thr Gln Ser Pro Ser Phe Leu Ser Ala Ser Val Gly
 1               5                  10                  15

Asp Arg Val Thr Ile Thr Cys Lys Ala Ser Gln Asp Val Arg Asn Thr
             20                  25                  30

Val Ala Trp Tyr Gln Gln Lys Thr Gly Lys Ala Pro Lys Leu Leu Ile
             35                  40                  45

Tyr Ser Ser Ser Tyr Arg Asn Thr Gly Val Pro Asp Arg Phe Thr Gly
         50                  55                  60
```

```
Ser Gly Ser Gly Thr Asp Phe Thr Leu Thr Ile Ser Ser Leu Gln Ala
 65                  70                  75                  80

Glu Asp Val Ala Val Tyr Phe Cys Gln Gln His Tyr Ile Thr Pro Tyr
                 85                  90                  95

Thr Phe Gly Gly Gly Thr Lys Val Glu Ile Lys
                100                 105

<210> SEQ ID NO 10
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk2 light chain variant

<400> SEQUENCE: 10

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Asp Val Arg Asn Thr
                 20                  25                  30

Val Ala Trp Tyr Gln Gln Lys Pro Gly Lys Ala Pro Lys Leu Leu Ile
             35                  40                  45

Tyr Ser Ser Ser Tyr Arg Asn Thr Gly Val Pro Asp Arg Phe Thr Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Phe Cys Gln Gln His Tyr Ile Thr Pro Tyr
                 85                  90                  95

Thr Phe Gly Gly Gly Thr Lys Val Glu Ile Lys
                100                 105

<210> SEQ ID NO 11
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk3 light chain variant

<400> SEQUENCE: 11

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Arg Asn Thr
                 20                  25                  30

Val Ala Trp Tyr Gln Gln Lys Pro Gly Lys Ala Pro Lys Leu Leu Ile
             35                  40                  45

Tyr Ser Ser Ser Tyr Arg Asn Thr Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Phe Cys Gln Gln His Tyr Ile Thr Pro Tyr
                 85                  90                  95

Thr Phe Gly Gly Gly Thr Lys Val Glu Ile Lys
                100                 105
```

```
<210> SEQ ID NO 12
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk4 light chain variant

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
        35                  40                  45

Tyr Ser Ser Tyr Arg Asn Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ile Thr Pro Tyr
                85                  90                  95

Thr Phe Gly Gly Gly Thr Lys Val Glu Ile Lys
            100                 105

<210> SEQ ID NO 13
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(10)
<223> OTHER INFORMATION: complementarity-determining region (CDR1) of
      heavy chain of anti-MMP9 antibody

<400> SEQUENCE: 13

Gly Phe Ser Leu Leu Ser Tyr Gly Val His
 1               5                  10

<210> SEQ ID NO 14
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(16)
<223> OTHER INFORMATION: complementarity-determining region (CDR2) of
      heavy chain of anti-MMP9 antibody

<400> SEQUENCE: 14

Val Ile Trp Thr Gly Gly Thr Thr Asn Tyr Asn Ser Ala Leu Met Ser
 1               5                  10                  15

<210> SEQ ID NO 15
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (1)...(7)
<223> OTHER INFORMATION: complementarity-determining region (CDR3) of
      heavy chain of anti-MMP9 antibody

<400> SEQUENCE: 15

Tyr Tyr Tyr Gly Met Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(11)
<223> OTHER INFORMATION: complementarity-determining region (CDR1) of
      light chain of anti-MMP9 antibody

<400> SEQUENCE: 16

Lys Ala Ser Gln Asp Val Arg Asn Thr Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(7)
<223> OTHER INFORMATION: complementarity-determining region (CDR2) of
      light chain of anti-MMP9 antibody

<400> SEQUENCE: 17

Ser Ser Ser Tyr Arg Asn Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(9)
<223> OTHER INFORMATION: complementarity-determining region (CDR3) of
      light chain of anti-MMP9 antibody

<400> SEQUENCE: 18

Gln Gln His Tyr Ile Thr Pro Tyr Thr
1               5

<210> SEQ ID NO 19
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH1 heavy chain
      amino acid sequence

<400> SEQUENCE: 19
caggtgcagc tgcaggaatc cggccctggc ctggtcaagc cctccgagac actgtccctg    60
```

```
acctgcaccg tgtccggctt ctccctgctg tcctacggcg tgcactgggt ccgacagcct    120
ccagggaagg gcctggaatg gctgggcgtg atctggaccg gcggcaccac caactacaac    180
tccgccctga tgtccggct gaccatctcc aaggacgact ccaagtccac cgtgtacctg    240
aagatgaact ccctgaaaac cgaggacacc gccatctact actgcgcccg gtactactac    300
ggcatggact actggggcca gggcacctcc gtgaccgtgt cctca                    345
```

```
<210> SEQ ID NO 20
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH2 heavy chain
      amino acid sequence

<400> SEQUENCE: 20
```

```
caggtgcagc tgcaggaatc cggccctggc ctggtcaagc cctccgagac actgtccctg    60
acctgcaccg tgtccggctt ctccctgctg tcctacggcg tgcactgggt ccgacagcct    120
ccaggcaaag gcctggaatg gctgggcgtg atctggaccg gcggcaccac caactacaac    180
tccgccctga tgtccggct gaccatctcc aaggacgact ccaagaacac cgtgtacctg    240
aagatgaact ccctgaaaac cgaggacacc gccatctact actgcgcccg gtactactac    300
ggcatggact actggggcca gggcaccctg gtcaccgtgt cctca                    345
```

```
<210> SEQ ID NO 21
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH3 heavy chain
      amino acid sequence

<400> SEQUENCE: 21
```

```
caggtgcagc tgcaggaatc cggccctggc ctggtcaagc cctccgagac actgtccctg    60
acctgcaccg tgtccggctt ctccctgctg tcctacggcg tgcactgggt ccgacagcct    120
ccaggcaaag gcctggaatg gctgggcgtg atctggaccg gcggcaccac caactacaac    180
tccgccctga tgtccggtt caccatctcc aaggacgact ccaagaacac cgtgtacctg    240
aagatgaact ccctgaaaac cgaggacacc gccatctact actgcgcccg gtactactac    300
ggcatggact actggggcca gggcaccctg gtcaccgtgt cctca                    345
```

```
<210> SEQ ID NO 22
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH4 heavy chain
      amino acid sequence

<400> SEQUENCE: 22
```

```
caggtgcagc tgcaggaatc cggccctggc ctggtcaagc cctccgagac actgtccctg    60
```

-continued

```
acctgcaccg tgtccggctt ctccctgctg tcctacggcg tgcactgggt ccgacagcct      120
ccaggcaaag gcctggaatg gctgggcgtg atctggaccg gcggcaccac caactacaac      180
tccgccctga tgtcccggtt caccatctcc aaggacgact ccaagaacac cctgtacctg      240
aagatgaact ccctgaaaac cgaggacacc gccatctact actgcgcccg gtactactac      300
ggcatggact actggggcca gggcaccctg gtcaccgtgt cctca                      345
```

```
<210> SEQ ID NO 23
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk1 light chain
      amino acid sequence

<400> SEQUENCE: 23
```

```
gacatcgtga tgacccagtc ccccagcttc ctgtccgcct ccgtgggcga cagagtgacc      60
atcacatgca aggcctctca ggacgtgcgg aacaccgtgg cctggtatca gcagaaaacc     120
ggcaaggccc ccaagctgct gatctactcc tcctcctacc ggaacaccgg cgtgcccgac     180
cggtttaccg gctctggctc cggcaccgac tttaccctga ccatcagctc cctgcaggcc     240
gaggacgtgg ccgtgtactt ctgccagcag cactacatca cccccctacac cttcggcgga    300 ggcaccaagg tggaaataaa a                                                321
```

```
<210> SEQ ID NO 24
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk2 light chain
      amino acid sequence

<400> SEQUENCE: 24
```

```
gacatcgtga tgacccagtc ccctccagc ctgtccgcct ctgtgggcga cagagtgacc       60
atcacatgca aggcctctca ggacgtgcgg aacaccgtgg cctggtatca gcagaagccc     120
ggcaaggccc ccaagctgct gatctactcc tcctcctacc ggaacaccgg cgtgcccgac     180
cggtttaccg gctctggctc cggcaccgac tttaccctga ccatcagctc cctgcaggcc     240
gaggacgtgg ccgtgtactt ctgccagcag cactacatca cccccctacac cttcggcgga    300 ggcaccaagg tggaaataaa a                                                321
```

```
<210> SEQ ID NO 25
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk3 light chain
      amino acid sequence

<400> SEQUENCE: 25
```

-continued

```
gacatccaga tgacccagtc ccctccagc ctgtccgcct ctgtgggcga cagagtgacc        60
atcacatgca aggcctccca ggacgtgcgg aacaccgtgg cctggtatca gcagaagccc       120
ggcaaggccc ccaagctgct gatctactcc tcctcctacc ggaacaccgg cgtgcccgac       180
cggttctctg gctctggaag cggcaccgac tttacccctg accatcagct cctgcaggcc       240
gaggacgtgg ccgtgtactt ctgccagcag cactacatca ccccctacac cttcggcgga      300
ggcaccaagg tggaaataaa a                                                321
```

```
<210> SEQ ID NO 26
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk4 light chain
      amino acid sequence

<400> SEQUENCE: 26
```

```
gacatccaga tgacccagtc ccctccagc ctgtccgcct ctgtgggcga cagagtgacc        60
atcacatgca aggcctctca ggacgtgcgg aacaccgtgg cctggtatca gcagaagccc       120
ggcaaggccc ccaagctgct gatctactcc tcctcctacc ggaacaccgg cgtgcccgac       180
cggttctctg gctctggaag cggcaccgac tttacccctg accatcagct cctgcaggcc       240
gaggacgtgg ccgtgtacta ctgccagcag cactacatca ccccctacac cttcggcgga      300
ggcaccaagg tggaaataaa a                                                321
```

```
<210> SEQ ID NO 27
<211> LENGTH: 707
<212> TYPE: PRT
<213> ORGANISM: Homo sapiens
<220> FEATURE:
<221> NAME/KEY: misc_feature
<222> LOCATION: (1)...(707)
<223> OTHER INFORMATION: matrix metalloproteinase 9 (MMP9)
<220> FEATURE:
<221> NAME/KEY: PEPTIDE
<222> LOCATION: (1)...(19)
<223> OTHER INFORMATION: signal peptide
<220> FEATURE:
<221> NAME/KEY: DOMAIN
<222> LOCATION: (38)...(98)
<223> OTHER INFORMATION: peptidoglycan binding domain
<220> FEATURE:
<221> NAME/KEY: SITE
<222> LOCATION: (98)...(99)
<223> OTHER INFORMATION: propeptide cleavage site
<220> FEATURE:
<221> NAME/KEY: DOMAIN
<222> LOCATION: (112)...(445)
<223> OTHER INFORMATION: Zn dependent metalloproteinase domain
<220> FEATURE:
<221> NAME/KEY: DOMAIN
<222> LOCATION: (223)...(271)
<223> OTHER INFORMATION: fibronectin type II domain (gelatin binding
      domain)
<220> FEATURE:
<221> NAME/KEY: DOMAIN
<222> LOCATION: (281)...(329)
<223> OTHER INFORMATION: fibronectin type II domain (gelatin binding
      domain)
<220> FEATURE:
<221> NAME/KEY: DOMAIN
<222> LOCATION: (340)...(388)
<223> OTHER INFORMATION: fibronectin type II domain (gelatin binding
      domain)
<220> FEATURE:
```

```
<221> NAME/KEY: misc_feature
<222> LOCATION: (400)...(411)
<223> OTHER INFORMATION: Zn binding region
<220> FEATURE:
<221> NAME/KEY: DOMAIN
<222> LOCATION: (521)...(565)
<223> OTHER INFORMATION: hemopexin-like domain
<220> FEATURE:
<221> NAME/KEY: DOMAIN
<222> LOCATION: (567)...(608)
<223> OTHER INFORMATION: hemopexin-like domain
<220> FEATURE:
<221> NAME/KEY: DOMAIN
<222> LOCATION: (613)...(659)
<223> OTHER INFORMATION: hemopexin-like domain
<220> FEATURE:
<221> NAME/KEY: DOMAIN
<222> LOCATION: (661)...(704)
<223> OTHER INFORMATION: hemopexin-like domain

<400> SEQUENCE: 27
```

| | | | | | | | | | | | | | | |
|---|---|---|---|---|---|---|---|---|---|---|---|---|---|---|
| Met | Ser | Leu | Trp | Gln | Pro | Leu | Val | Leu | Val | Leu | Leu | Val | Leu | Gly | Cys |
| 1 | | | | 5 | | | | | 10 | | | | | 15 | |
| Cys | Phe | Ala | Ala | Pro | Arg | Gln | Arg | Gln | Ser | Thr | Leu | Val | Leu | Phe | Pro |
| | | | 20 | | | | | 25 | | | | | 30 | | |
| Gly | Asp | Leu | Arg | Thr | Asn | Leu | Thr | Asp | Arg | Gln | Leu | Ala | Glu | Glu | Tyr |
| | | | 35 | | | | | 40 | | | | | 45 | | |
| Leu | Tyr | Arg | Tyr | Gly | Tyr | Thr | Arg | Val | Ala | Glu | Met | Arg | Gly | Glu | Ser |
| | 50 | | | | | 55 | | | | | 60 | | | | |
| Lys | Ser | Leu | Gly | Pro | Ala | Leu | Leu | Leu | Leu | Gln | Lys | Gln | Leu | Ser | Leu |
| 65 | | | | | 70 | | | | | 75 | | | | | 80 |
| Pro | Glu | Thr | Gly | Glu | Leu | Asp | Ser | Ala | Thr | Leu | Lys | Ala | Met | Arg | Thr |
| | | | | 85 | | | | | 90 | | | | | 95 | |
| Pro | Arg | Cys | Gly | Val | Pro | Asp | Leu | Gly | Arg | Phe | Gln | Thr | Phe | Glu | Gly |
| | | | 100 | | | | | 105 | | | | | 110 | | |
| Asp | Leu | Lys | Trp | His | His | His | Asn | Ile | Thr | Tyr | Trp | Ile | Gln | Asn | Tyr |
| | | | 115 | | | | | 120 | | | | | 125 | | |
| Ser | Glu | Asp | Leu | Pro | Arg | Ala | Val | Ile | Asp | Asp | Ala | Phe | Ala | Arg | Ala |
| | 130 | | | | | 135 | | | | | 140 | | | | |
| Phe | Ala | Leu | Trp | Ser | Ala | Val | Thr | Pro | Leu | Thr | Phe | Thr | Arg | Val | Tyr |
| 145 | | | | | 150 | | | | | 155 | | | | | 160 |
| Ser | Arg | Asp | Ala | Asp | Ile | Val | Ile | Gln | Phe | Gly | Val | Ala | Glu | His | Gly |
| | | | | 165 | | | | | 170 | | | | | 175 | |
| Asp | Gly | Tyr | Pro | Phe | Asp | Gly | Lys | Asp | Gly | Leu | Leu | Ala | His | Ala | Phe |
| | | | 180 | | | | | 185 | | | | | 190 | | |
| Pro | Pro | Gly | Pro | Gly | Ile | Gln | Gly | Asp | Ala | His | Phe | Asp | Asp | Asp | Glu |
| | | | 195 | | | | | 200 | | | | | 205 | | |
| Leu | Trp | Ser | Leu | Gly | Lys | Gly | Val | Val | Val | Pro | Thr | Arg | Phe | Gly | Asn |
| | 210 | | | | | 215 | | | | | 220 | | | | |
| Ala | Asp | Gly | Ala | Ala | Cys | His | Phe | Pro | Phe | Ile | Phe | Glu | Gly | Arg | Ser |
| 225 | | | | | 230 | | | | | 235 | | | | | 240 |
| Tyr | Ser | Ala | Cys | Thr | Thr | Asp | Gly | Arg | Ser | Asp | Gly | Leu | Pro | Trp | Cys |
| | | | | 245 | | | | | 250 | | | | | 255 | |
| Ser | Thr | Thr | Ala | Asn | Tyr | Asp | Thr | Asp | Asp | Arg | Phe | Gly | Phe | Cys | Pro |
| | | | 260 | | | | | 265 | | | | | 270 | | |
| Ser | Glu | Arg | Leu | Tyr | Thr | Arg | Asp | Gly | Asn | Ala | Asp | Gly | Lys | Pro | Cys |
| | | | 275 | | | | | 280 | | | | | 285 | | |
| Gln | Phe | Pro | Phe | Ile | Phe | Gln | Gly | Gln | Ser | Tyr | Ser | Ala | Cys | Thr | Thr |
| | 290 | | | | | 295 | | | | | 300 | | | | |
| Asp | Gly | Arg | Ser | Asp | Gly | Tyr | Arg | Trp | Cys | Ala | Thr | Thr | Ala | Asn | Tyr |

```
            305                 310                 315                 320
Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
                355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
                435                 440                 445

Pro Glu Pro Arg Pro Pro Thr Thr Thr Pro Gln Pro Thr Ala Pro
                450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
                530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705

<210> SEQ ID NO 28
<211> LENGTH: 687
```

```
<212> TYPE: PRT
<213> ORGANISM: Homo sapiens
<220> FEATURE:
<221> NAME/KEY: misc_feature
<222> LOCATION: (1)...(687)
<223> OTHER INFORMATION: mature full-length matrix metalloproteinase 9
      (MMP9)

<400> SEQUENCE: 28

Pro Arg Gln Arg Gln Ser Thr Leu Val Leu Phe Pro Gly Asp Leu Arg
 1               5                  10                  15

Thr Asn Leu Thr Asp Arg Gln Leu Ala Glu Glu Tyr Leu Tyr Arg Tyr
             20                  25                  30

Gly Tyr Thr Arg Val Ala Glu Met Arg Gly Glu Ser Lys Ser Leu Gly
         35                  40                  45

Pro Ala Leu Leu Leu Leu Gln Lys Gln Leu Ser Leu Pro Glu Thr Gly
     50                  55                  60

Glu Leu Asp Ser Ala Thr Leu Lys Ala Met Arg Thr Pro Arg Cys Gly
65                  70                  75                  80

Val Pro Asp Leu Gly Arg Phe Gln Thr Phe Glu Gly Asp Leu Lys Trp
                 85                  90                  95

His His His Asn Ile Thr Tyr Trp Ile Gln Asn Tyr Ser Glu Asp Leu
            100                 105                 110

Pro Arg Ala Val Ile Asp Asp Ala Phe Ala Arg Ala Phe Ala Leu Trp
        115                 120                 125

Ser Ala Val Thr Pro Leu Thr Phe Thr Arg Val Tyr Ser Arg Asp Ala
    130                 135                 140

Asp Ile Val Ile Gln Phe Gly Val Ala Glu His Gly Asp Gly Tyr Pro
145                 150                 155                 160

Phe Asp Gly Lys Asp Gly Leu Leu Ala His Ala Phe Pro Pro Gly Pro
                165                 170                 175

Gly Ile Gln Gly Asp Ala His Phe Asp Asp Asp Glu Leu Trp Ser Leu
            180                 185                 190

Gly Lys Gly Val Val Val Pro Thr Arg Phe Gly Asn Ala Asp Gly Ala
        195                 200                 205

Ala Cys His Phe Pro Phe Ile Phe Glu Gly Arg Ser Tyr Ser Ala Cys
    210                 215                 220

Thr Thr Asp Gly Arg Ser Asp Gly Leu Pro Trp Cys Ser Thr Thr Ala
225                 230                 235                 240

Asn Tyr Asp Thr Asp Asp Arg Phe Gly Phe Cys Pro Ser Glu Arg Leu
                245                 250                 255

Tyr Thr Arg Asp Gly Asn Ala Asp Gly Lys Pro Cys Gln Phe Pro Phe
            260                 265                 270

Ile Phe Gln Gly Gln Ser Tyr Ser Ala Cys Thr Thr Asp Gly Arg Ser
        275                 280                 285

Asp Gly Tyr Arg Trp Cys Ala Thr Thr Ala Asn Tyr Asp Arg Asp Lys
    290                 295                 300

Leu Phe Gly Phe Cys Pro Thr Arg Ala Asp Ser Thr Val Met Gly Gly
305                 310                 315                 320

Asn Ser Ala Gly Glu Leu Cys Val Phe Pro Phe Thr Phe Leu Gly Lys
                325                 330                 335

Glu Tyr Ser Thr Cys Thr Ser Glu Gly Arg Gly Asp Gly Arg Leu Trp
            340                 345                 350

Cys Ala Thr Thr Ser Asn Phe Asp Ser Asp Lys Lys Trp Gly Phe Cys
        355                 360                 365

Pro Asp Gln Gly Tyr Ser Leu Phe Leu Val Ala Ala His Glu Phe Gly
```

```
            370                 375                 380
His Ala Leu Gly Leu Asp His Ser Ser Val Pro Glu Ala Leu Met Tyr
385                 390                 395                 400

Pro Met Tyr Arg Phe Thr Glu Gly Pro Pro Leu His Lys Asp Asp Val
                405                 410                 415

Asn Gly Ile Arg His Leu Tyr Gly Pro Arg Pro Glu Pro Glu Pro Arg
            420                 425                 430

Pro Pro Thr Thr Thr Thr Pro Gln Pro Thr Ala Pro Pro Thr Val Cys
        435                 440                 445

Pro Thr Gly Pro Pro Thr Val His Pro Ser Glu Arg Pro Thr Ala Gly
450                 455                 460

Pro Thr Gly Pro Pro Ser Ala Gly Pro Thr Gly Pro Pro Thr Ala Gly
465                 470                 475                 480

Pro Ser Thr Ala Thr Thr Val Pro Leu Ser Pro Val Asp Asp Ala Cys
                485                 490                 495

Asn Val Asn Ile Phe Asp Ala Ile Ala Glu Ile Gly Asn Gln Leu Tyr
            500                 505                 510

Leu Phe Lys Asp Gly Lys Tyr Trp Arg Phe Ser Glu Gly Arg Gly Ser
        515                 520                 525

Arg Pro Gln Gly Pro Phe Leu Ile Ala Asp Lys Trp Pro Ala Leu Pro
530                 535                 540

Arg Lys Leu Asp Ser Val Phe Glu Glu Pro Leu Ser Lys Lys Leu Phe
545                 550                 555                 560

Phe Phe Ser Gly Arg Gln Val Trp Val Tyr Thr Gly Ala Ser Val Leu
                565                 570                 575

Gly Pro Arg Arg Leu Asp Lys Leu Gly Leu Gly Ala Asp Val Ala Gln
            580                 585                 590

Val Thr Gly Ala Leu Arg Ser Gly Arg Gly Lys Met Leu Leu Phe Ser
        595                 600                 605

Gly Arg Arg Leu Trp Arg Phe Asp Val Lys Ala Gln Met Val Asp Pro
610                 615                 620

Arg Ser Ala Ser Glu Val Asp Arg Met Phe Pro Gly Val Pro Leu Asp
625                 630                 635                 640

Thr His Asp Val Phe Gln Tyr Arg Glu Lys Ala Tyr Phe Cys Gln Asp
                645                 650                 655

Arg Phe Tyr Trp Arg Val Ser Ser Arg Ser Glu Leu Asn Gln Val Asp
            660                 665                 670

Gln Val Gly Tyr Val Thr Tyr Asp Ile Leu Gln Cys Pro Glu Asp
        675                 680                 685

<210> SEQ ID NO 29
<211> LENGTH: 20
<212> TYPE: PRT
<213> ORGANISM: Homo sapiens
<220> FEATURE:
<221> NAME/KEY: PEPTIDE
<222> LOCATION: (1)...(20)
<223> OTHER INFORMATION: matrix metalloproteinase 9 (MMP9) signal
      peptide

<400> SEQUENCE: 29

Met Ser Leu Trp Gln Pro Leu Val Leu Val Leu Leu Val Leu Gly Cys
1               5                   10                  15

Cys Phe Ala Ala
            20
```